United States Patent
Park et al.

(10) Patent No.: US 8,934,971 B1
(45) Date of Patent: Jan. 13, 2015

(54) IMPLANTABLE CARDIAC STIMULATION DEVICE AND METHOD THAT STABILIZES VENTRICULAR RATE DURING EPISODES OF ATRIAL FIBRILLATION

(75) Inventors: Euljoon Park, Valencia, CA (US); You-Ho Kim, Seoul (KR); Taraneh Ghaffari Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 1807 days.

(21) Appl. No.: 11/940,174

(22) Filed: Nov. 14, 2007

(51) Int. Cl.
*A61N 1/00* (2006.01)

(52) U.S. Cl.
USPC .......................................................... 607/17

(58) Field of Classification Search
None
See application file for complete search history.

(56) References Cited

U.S. PATENT DOCUMENTS

| | | | |
|---|---|---|---|
| 5,356,425 A | 10/1994 | Bardy et al. | |
| 5,411,531 A | 5/1995 | Hill et al. | |
| 5,507,784 A | 4/1996 | Hill et al. | |
| 6,256,537 B1 | 7/2001 | Stoop et al. | |

FOREIGN PATENT DOCUMENTS

| | | |
|---|---|---|
| EP | 0647149 B1 | 1/1997 |
| WO | WO 94/00190 | 1/1994 |
| WO | WO 97/40880 | 11/1997 |

*Primary Examiner* — Christopher D Koharski
*Assistant Examiner* — Elizabeth K So

(57) ABSTRACT

An implantable cardiac stimulation device and method provide electrical stimulation therapy to stabilize the ventricular rate of a heart during episodes of atrial fibrillation. The stimulation therapy may be a plurality of stimulation pulses delivered to the AV node during the AV node refractory period following the sensing of an atrial event. Alternatively, the stimulation therapy may be a plurality of sub-threshold stimulation pulses delivered to capture AV node vagal innervations following the detection of atrial fibrillation.

7 Claims, 5 Drawing Sheets

IMPLANTABLE CARDIAC STIMULATION DEVICE AND METHOD THAT STABILIZES VENTRICULAR RATE DURING EPISODES OF ATRIAL FIBRILLATION

FIELD OF THE INVENTION

The present invention generally relates to an implantable cardiac stimulation device and method that provides electrical therapy to a patient's heart. The present invention more particularly relates to such a device and method that provides electrical stimulation therapy to stabilize ventricular rate of a heart during episodes of atrial fibrillation.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or evoked responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or evoked responses are sensed between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators (ICD's) are also well known in the art. These devices generally include an arrhythmia detector that detects accelerated arrhythmias, such as tachycardia or fibrillation. When such a tachyarrhythmia is detected, a pulse generator delivers electrical therapy to the patient's heart. A therapy for tachycardia may be anti-tachycardia pacing and a therapy for fibrillation may be a defibrillating shock. Such therapies for both atrial and ventricular tachyarrhythmias are well known.

With ventricular tachycardia (VT) the ventricles of the heart beat abnormally fast. Though often unpleasant for the patient, a ventricular tachycardia is typically not immediately fatal. However, ventricular fibrillation (VF) is an immediately life threatening tachyarrhythmia for which the device takes immediate and aggressive action. Such action is required because during VF, the heart beats chaotically such that there is little or no net flow of blood from the heart to the brain and other organs.

With atrial tachycardia (AT), the atria of the heart beat rapidly at an abnormally high rate. This can cause the ventricular to in turn beat at a high rate. Cardiac output is reduced. The patient may experience dizziness or feel fatigued. Although not immediately life threatening, it can also be unpleasant to a patient.

Atrial fibrillation (AF) is a common atrial tachyarrhythmia and can occur suddenly. It results in rapid and chaotic activity of the atria of the heart. The chaotic atrial activity in turn causes the ventricular activity to become rapid and chaotic. Under these conditions, patients also experience dizziness or feel fatigued due to reduced cardiac output. Normal daily activities must be suspended. Although not life threatening, AF is associated with strokes thought to be caused by blood clots forming in areas of stagnant blood flow as a result of prolonged atrial fibrillation. In addition to strokes, symptoms of atrial fibrillation may include fatigue, syncope, congestive heart failure, weakness and dizziness.

Stabilizing the ventricular rhythm during episodes of AF is of great concern. A stabilized ventricular rate during episodes of AF would add greatly to the quality of life of such patients. Drugs are known which can assist some patients toward a more stable ventricular rate during episodes of AF. Unfortunately, many patients with chronic AF are resistant to such drugs. One therapy for such patients is to ablate their atrioventricular (AV) node. The AV node is a small concentration of specialized connective tissue at the base of the atrial septum which transmits signals from the atria to the ventricles. When a cardiac cycle of the heart is initialized, an electrical signal first causes the atria to be activated (contract) and then, after being transmitted by the AV node and conducted to the ventricles, causes the ventricles to be activated (contract). The time between the atrial activation and the ventricular activation is referred to as an AV interval. Ablation of the AV node thus destroys the AV nodal function of transmitting the electrical signals from the atria to the ventricles. These patients are pacemaker dependent in that they must receive and maintain a pacemaker implant to pace the ventricles During episodes of AF, the ventricles continue to be paced at an appropriate rate independent of the rapid and chaotic atrial rate.

An alternative albeit experimental approach was to ablate only parts of the atrium to block conduction from the atrium to the AV node and to place a lead in the AV node or His Bundle. While the ventricles were captured, significant parts of the atrium needed to be ablated.

It would thus be desirable if the ventricular rate could be stabilized during episodes of AF towards preserving normal conduction patterns in the ventricles without the need for ablation The present invention addresses these and other issues.

SUMMARY OF THE INVENTION

In one embodiment, an implantable cardiac stimulation device comprises a first sensing circuit that senses atrial activity of a heart and a pulse generator that, responsive to the first sensing circuit sensing an atrial event, delivers a plurality of stimulation pulses to the AV node of the heart during an AV nodal refractory period following the sensed atrial event.

The pulse generator may be arranged to provide the stimulation pulses with an energy above the atrial capture threshold of the heart. The pulse generator also be arranged to provide the plurality of stimulation pulses during an interval having a duration related to a desired ventricular rate of the heart. The device may further comprise a second sensing circuit that senses ventricular activity of the heart to monitor ventricular rate.

The device may further comprise an atrial fibrillation detector and the pulse generator may be enabled upon detection of atrial fibrillation.

In another embodiment, an implantable cardiac stimulation device comprises a first sensing circuit that senses atrial activity of a heart, a second sensing circuit that senses ventricular activity of the heart to monitor ventricular rate, and an atrial fibrillation detector that detects atrial fibrillation of the heart. The device further comprises a pulse generator that, responsive to the atrial fibrillation detector detecting atrial fibrillation of the heart and the first sensing circuit sensing an atrial event, delivers a plurality of stimulation pulses to the AV node of the heart during an AV nodal refractory period following the sensed atrial event during an interval having a duration related to a desired ventricular rate of the heart.

In a further embodiment, an implantable cardiac stimulation device comprises an atrial fibrillation detector that detects atrial fibrillation of a heart, and a pulse generator that, responsive to the atrial fibrillation detector detecting atrial fibrillation of the heart, delivers a plurality of neural stimulation pulses to near the AV node of the heart to capture vagal innervations to the AV node during a time period having a duration related to a desired ventricular rate of the heart.

The pulse generator may be arranged to provide the neural stimulation pulses with an energy and/or frequency that avoids capture of the heart. The device may further comprises a sensing circuit that senses ventricular activity of the heart to monitor ventricular rate.

The pulse generator may be arranged to provide the neural stimulation pulses during successive time periods, each having a duration related to a desired ventricular rate of the heart. The immediately successive time periods may be separated by time intervals sufficient to permit a single atrial event to be issued by the heart.

In another embodiment, a method for use in an implantable cardiac stimulation device comprises sensing atrial activity of a heart and responsive to the sensing of an atrial event, delivering a plurality of stimulation pulses to the AV node of the heart during an AV nodal refractory period following the sensed atrial event.

The providing step may include providing the stimulation pulses with an energy above the atrial capture threshold of the heart. The providing step may further include providing the plurality of stimulation pulses during an interval having a duration related to a desired ventricular rate of the heart.

The method may further comprise the steps of sensing ventricular activity of the heart and monitoring ventricular rate. The method may further comprise the step of detecting atrial fibrillation before providing the stimulation pulses. The stimulation pulses may have an energy above the atrial capture threshold of the heart.

In a still further embodiment, a method for use in an implantable cardiac stimulation device, comprises detecting atrial fibrillation of a heart and responsive to detecting atrial fibrillation of the heart, delivering a plurality of neural stimulation pulses to near the AV node of the heart to capture vagal innervations to the AV node during a time period having a duration related to a desired ventricular rate of the heart.

The neural stimulation pulses may be provided with an energy and/or frequency that avoids capture of the heart.

The method may further comprise the steps of sensing ventricular activity of the heart and monitoring ventricular rate. The neural stimulation pulses may be provided during successive time periods, each having a duration related to a desired ventricular rate of the heart. Immediately successive time periods may be separated by time intervals sufficient to permit a single atrial event to be issued by the heart.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
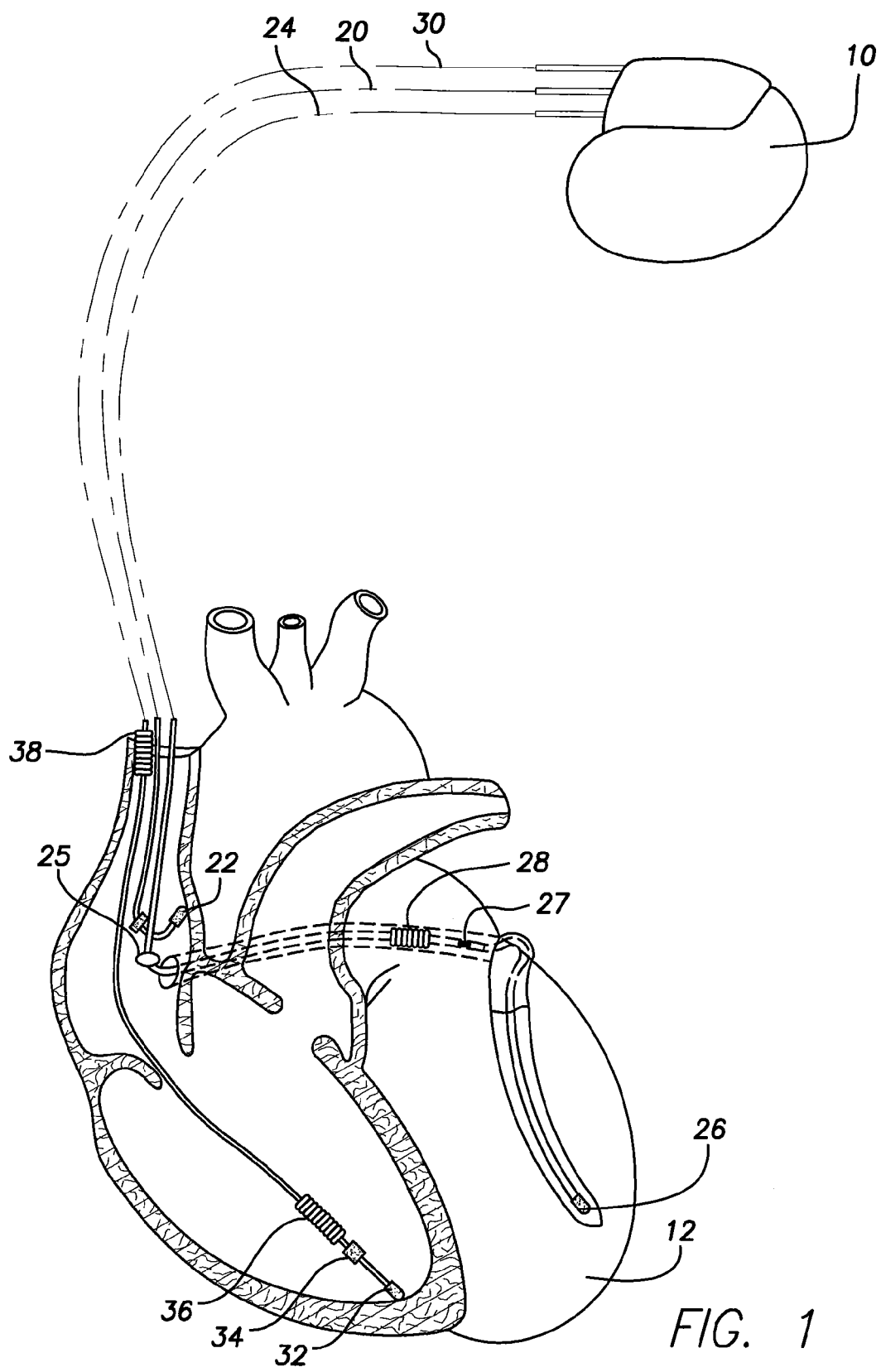
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The electrode 22, in accordance with an embodiment of the invention, may also be used to apply stimulation pulses to the AV node to extend the AV nodal refractory period.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. The lead 24 includes a further electrode 25 which is placed near to the coronary sinus ostium. The electrode 25 is thus suited for use in either delivering stimulation pulses to the AV node or for delivering stimulation to the vagal nerves in close proximity to the AV node.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
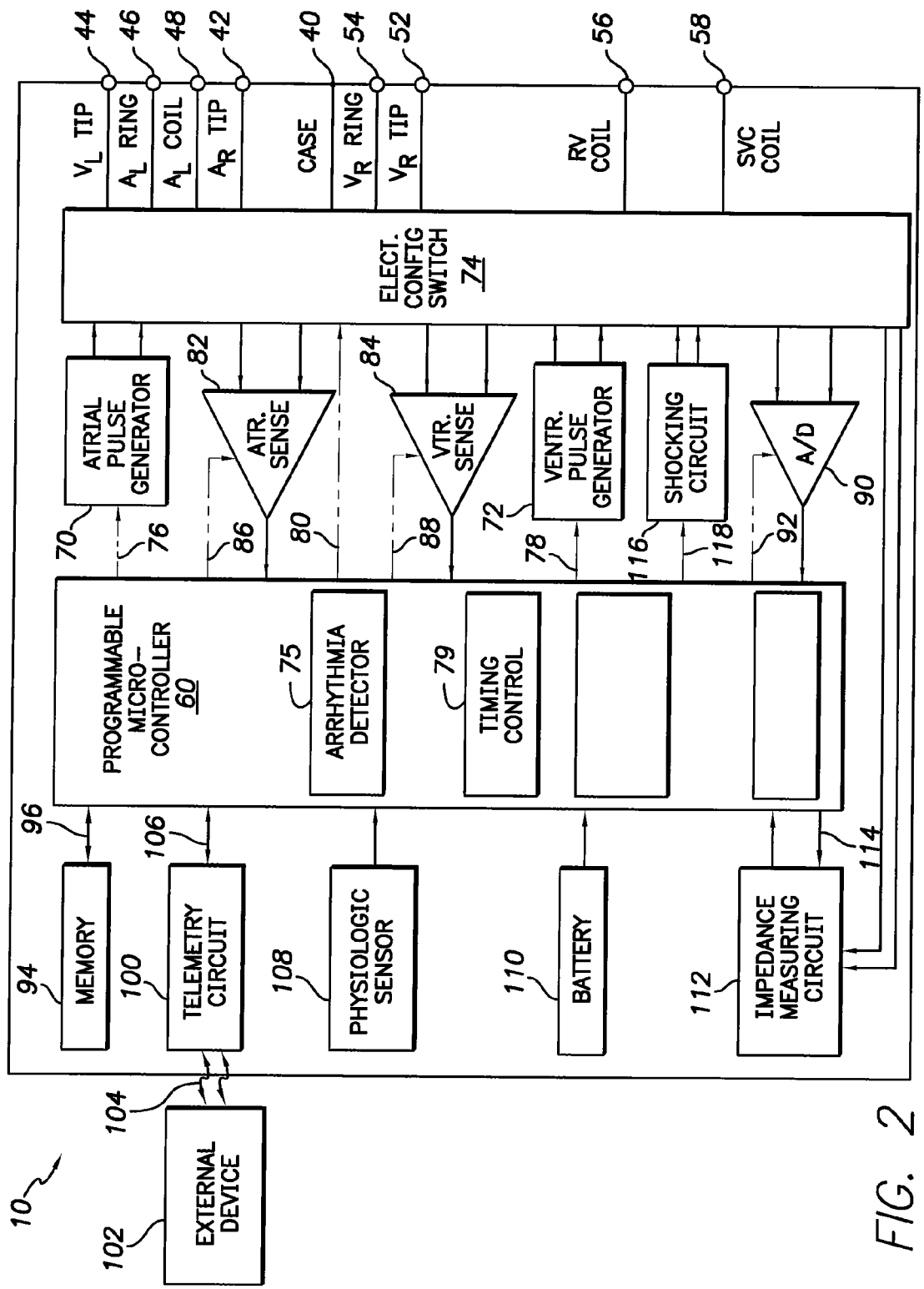
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. Either one of the pulse generators 70 and 72 may be employed for delivering stimulation pulses to or near to the AV node via electrode 22 or electrode 25.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. The timing control 79 may further be employed to time periods as, for example, the time periods in which stimulation pulses are applied for extending the AV nodal refractory period and other time periods associated with stabilization of the ventricular rate during episodes of AF. To that end, the timing control may control the time between individual pulses and the total time in which the pulse are delivered. The timing control 79 may further be used determine ventricular rate, for example.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. The ventricular sensing circuits 84, in accordance with the embodiments of the invention described herein, may be used to sense ventricular activity for monitoring ventricular rate. Such monitoring is helpful in setting certain AV node stimulation time periods as will be described subsequently.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, may receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

The device 10 further includes an arrhythmia detector 75 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). As will be seen subsequently, in the embodiments described herein, detection of AF is a prerequisite to the ventricular rate stabilizing therapy.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. In this regard, the sensor 108 may be employed to set AV node stimulation time periods to control the stabilized ventricular rate, as will be described subsequently. The physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with the broader aspects of the invention, to stabilize the ventricular rate during episodes of AF, the AV node is essentially turned "OFF" and "ON" periodically to limit the conduction of atrial pulses to the ventricle. The AV node is turned off by increasing its refractoriness through electrical stimulation. This may be accomplished by a lead placement on or in close proximity to the AV node. More specifically, this may be accomplished by an endocardial lead such as lead 20 having an electrode 22 in the atrium or a CS lead, such as lead 24, having electrode 25 in the vicinity of the CS ostium.

In accordance with a first embodiment, the AV nodal refractoriness may be lengthened by delivering a series of pacing-like stimulation pulses during the AV node refractory period, thereby extending its interval. Preferably, the frequency of the AV nodal pacing is slightly higher than $$\frac{1}{AVRP},$$

where AVRP is the AV nodal refractory period.

In another embodiment, continuous stimulation pulses (for neural stimulation) are delivered to stimulate the distal end of vagal nerves of the AV node. The bursts of stimulation pulses are preferably sub-threshold so that the heart is not captured by the pulses delivered near the AV node. The duty cycle of the bursts may be programmable to achieve the target ventricular rate.

To re-establish AV nodal conduction (turn the AV node back ON), the electrical stimulation of the node itself or the vagal innervations are temporarily stopped. The duration of this period is selected such that only one atrial activation passes through the AV node before the node is turned back to OFF again. This will promote the intrinsic conduction and contractile function in the ventricle.

The same lead for AV nodal stimulation or a different lead may have another electrode or pair of electrodes to detect atrial events. For example, if electrode 25 is used to deliver the stimulation pulses, electrode 22 may be employed to sense atrial events. Conversely, if electrode 22 is used to deliver the stimulation pulses, electrode 25 may be employed to sense atrial events. The ventricular rate may be determined by the total refractory period of the AV node and the time in which the AV node is opened. As previously mentioned, the ventricular rate may be controlled by physiological sensor 108 within the device 10.

Figure 3:
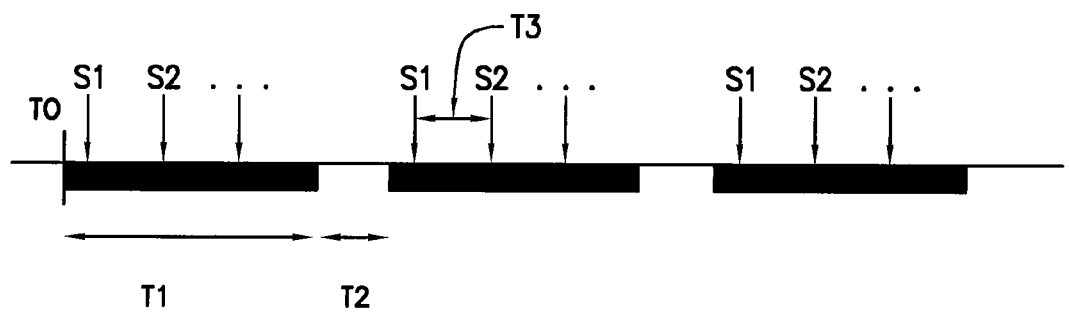
FIG. 3 is a timing diagram illustrating a first embodiment of the invention wherein stimulation pulses are delivered to the AV node in synchronism with a sensed atrial event.

The timing diagram of FIG. 3 illustrates the manner in which the AV node may be stimulated to extend its refractory period during episodes of AF to stabilize the ventricular rate. Once AF is diagnosed by the device, an algorithm is activated to control the timing and duration of the stimulation to the AV node region. At T0, an atrial event at the AV node is sensed. After a pause (the time between T0 and S1), the stimulation to the node is initiated. The stimulation comprises a plurality of stimulation pulses (S1, S2, . . . ). The ventricular signal is monitored to ensure that the conducted beat captured the ventricles. The stimulation to the node will continue during time period T1 which is set depending on the ventricular rate desired. Specifically, the duration of the stimulation (in ms) following a single atrial pulse is calculated by:

$$\frac{60{,}000}{V_{rate}} - k$$

where $80 \leq k \leq 200$.

The delivery of the series of pacing pulses extends the AV nodal refractoriness. The AV nodal refractory period is controlled by the coupling interval T3 and the number of the stimulation pulses. The opening period T2 is selected to be short enough to pass only the first conduction from the atrium. The ventricular rate and stability is thus controlled by T1+T2. T1+T2 can be modulated by physiologic sensor 108. Also, because the AV node is refractory, the stimulation pulses may have an energy above the atrial capture threshold of the heart.

Figure 4:
FIG. 4 is another timing diagram illustrating a second embodiment of the invention wherein stimulation pulses are delivered to vagal nerves for extending the AV nodal refractory period of a heart during AF.

FIG. 4 shows a timing diagram illustrating a second embodiment to extend the AV nodal refractory period during episodes of AF to stabilize the ventricular rate. During T1, a plurality of stimulation pulses are delivered to stimulate the distal ends of vagal nerves in close proximity to the AV node. The opening period T2 is selected to pass only the first conduction from the atrium. The ventricular rate and stability is controlled by T1+T2. As previously mentioned, T1+T2 may be modulated by physiologic sensor 108. Preferably, the pulses have an energy and/or frequency that is sub-threshold and thus not capable of capturing the atria. The stimulation thus need not be delivered synchronously to a sensed atrial event.

Figure 5:
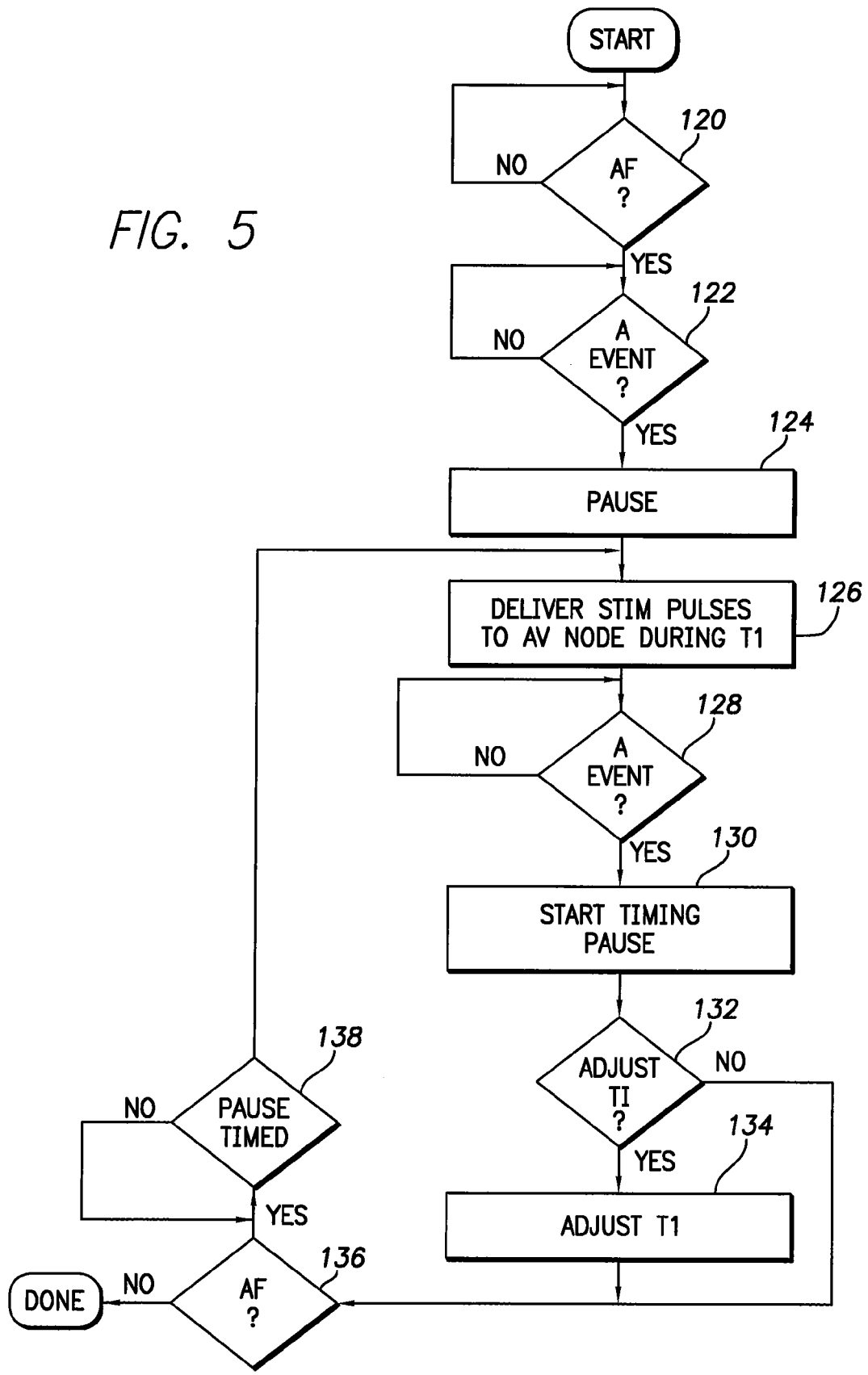
FIG. 5 is a flow chart describing an overview of the operation of the first embodiment of the present invention.

In FIG. 5, a flow chart is shown describing an overview of the operation and novel features implemented in one embodiment of the device 10. In this flow chart, and the other flow chart of FIG. 6 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 5 is directed to the first mentioned embodiment wherein the AV nodal refractory period is extended to stabilize the ventricular rate during episodes of AF by delivering a plurality of pacing-like stimulation pulses to the AV node after a first atrial event is sensed and for a time related to a desired ventricular rate. The process initiates with decision block 120 wherein AF is initially detected by the arrhythmia detector 75. Once AF is detected, the process proceeds to decision block 122 for the sensing of the first atrial event following the detection of AF. Next, the process advances to activity block 124 where a pause is timed. The pause is implemented to allow the sensed atrial event to be transmitted from the AV node. The pause may have a duration, for example, of between 5 and 15 milliseconds.

After the pause, the process advances to activity block 126 wherein a plurality of stimulation pulses are delivered to the AV node. Since the AV node is refractory, the pulses may have an energy above the capture threshold of the atria. The pulse are delivered during a time period T1 as shown in FIG. 3 and with a frequency as previously explained. The pulses may be delivered to the right atrium with an electrode such as electrode 22 of lead 20 or electrode 25 of lead 24 (FIG. 1).

After the stimulation pulses are delivered, the process proceeds to decision block 128 where, during a time period T2, The first atrial event of the next cardiac cycle is sensed. The time period T2 is selected so that only a single atrial event occurs during that time period. Next, in activity block 130, the timing control starts timing the pause. Once the timing of the pause is begun and during the pause timing, it is determined in decision block if an adjustment in T1 is required. Such an adjustment may be dictated by the output of an activity sensor, such as sensor 108, calling for an increased or decreased ventricular rate. If adjustment of T1 is required, that adjustment may be made in accordance with activity block 134. The process then proceeds to decision block 136 where it is determined if the AF episode persists or has terminated. If the AF episode has terminated, the process completes. If not, the process then determines if the pause has been fully timed. When it has, the process returns to activity block 126 for the delivery of the next plurality of stimulation pulses to the AV node.

Figure 6:
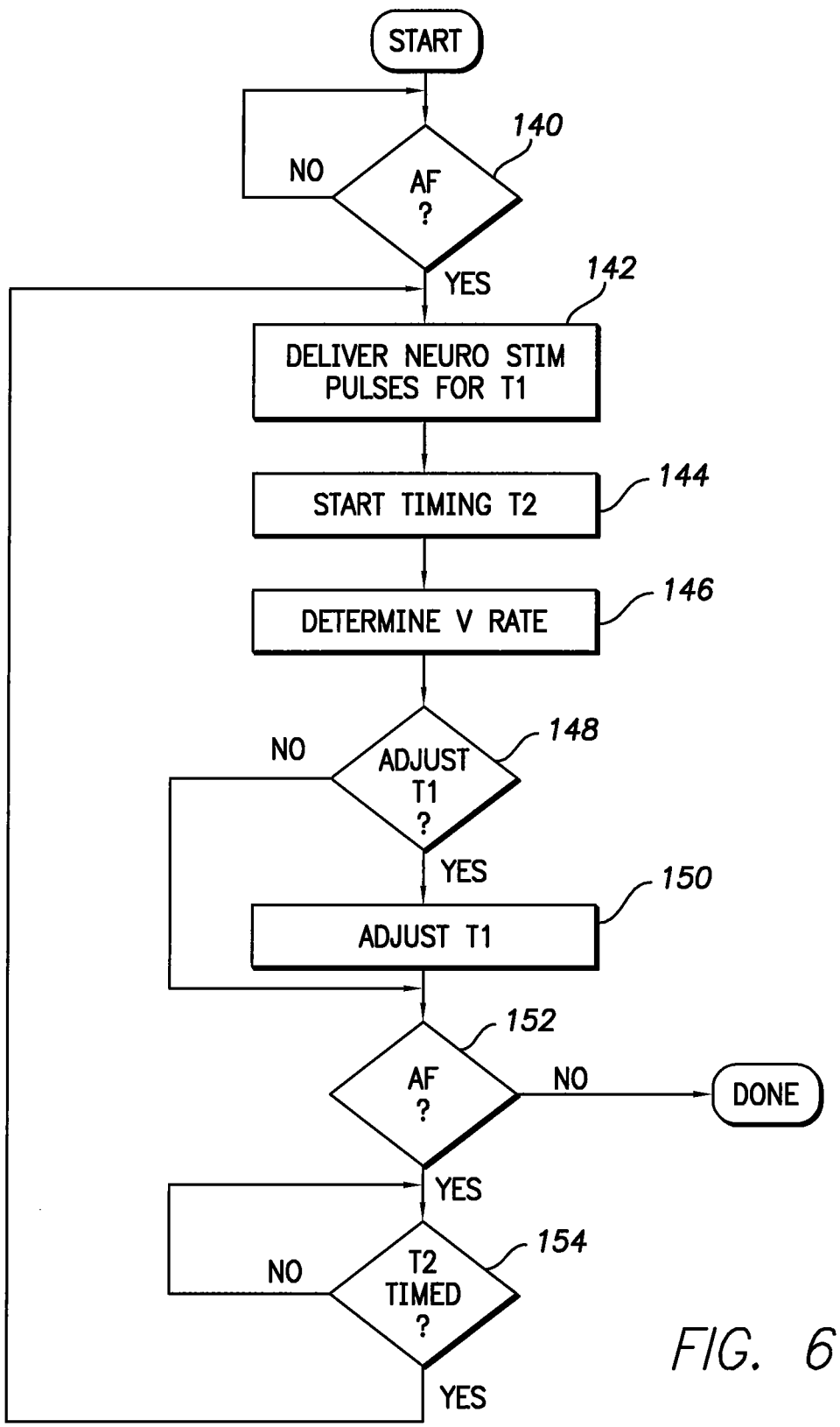
FIG. 6 is a flow chart describing an overview of the operation of the second embodiment of the present invention.

The process of FIG. 6 is directed to the second mentioned embodiment wherein the vagal nerves associated with the AV node are stimulated to capture vagal innervations and stabilize the ventricular rate during episodes of AF. Here, a plurality of sub-threshold stimulation pulses are delivered to near the AV node after detection of AF for a time related to a desired ventricular rate. The process initiates with decision block 140 wherein AF is initially detected by the arrhythmia detector 75. Once AF is detected, the process advances to activity block 142 wherein a plurality of stimulation pulses are delivered to near the AV node. Since the AV node may not be refractory, the pulses preferably have an energy and/or frequency below the capture threshold of the atria. The pulses are delivered during a time period T1 as shown in FIG. 4. The pulses may be delivered to near the AV node with electrode 25 of lead 24 positioned near to the coronary sinus ostium (FIG. 1).

After the stimulation pulses are delivered, the process proceeds to activity block 144 where the timing control starts timing the time period T2 of FIG. 4. The time period T2 is preferably selected such that only one atrial event occurs during the time period T2. Once the timing of the time period T2 is begun, and during the time period T2, the ventricular rate is first determined in activity block 146. To support this function, the ventricular activity is sensed by sensing circuit 84. Next, in decision block 148, it is determined from the ventricular rate and other factors, such the output of sensor 108, if the time period T1 needs adjustment. If adjustment of T1 is required, that adjustment may be made in accordance with activity block 150. The process then proceeds to decision block 152 where it is determined if the AF episode has persisted or has terminated. If the AF episode has terminated, the process completes. If not, the process then determines if the time period T2 has been fully timed. When it has, the process returns to activity block 142 for the delivery of the next plurality of stimulation pulses to capture the vagal innervations and the process repeats.

Thus, as may be seen from the forgoing, the present invention permits the ventricular rate to be stabilized during episodes of AF without requiring ablation of the AV node or significant portions of the atria. The stabilization is performed safely by delivery of stimulation pulses during the AV node refractory period or with an energy and/or frequency incapable of capturing the heart.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
a first sensing circuit that senses atrial activity of a heart; and
a pulse generator that, responsive to the first sensing circuit sensing an AF episode, initiates delivery of a first plurality of stimulation pulses to the AV node of the heart during an AV nodal refractory period following the sensed AF episode;
wherein the pulse generator is arranged to provide the stimulation pulses with an energy above the atrial capture threshold of the heart to extend the AV nodal refractory period; and
wherein after the plurality of first stimulation pulses are delivered, a first atrial event of a next cardiac cycle is sensed and a time period T2 is selected so that only a single atrial event occurs during that time period T2, and wherein if it is determined that the AF episode is not terminated, the pulse generator delivers a second plurality of stimulation pulses to the AV node of the heart at the completion of the time period T2.

2. The device of claim 1, wherein the pulse generator is arranged to provide the plurality of stimulation pulses during an interval having a duration related to a desired ventricular rate of the heart.

3. The device of claim 2, further comprising a second sensing circuit that senses ventricular activity of the heart to monitor ventricular rate.

4. An implantable cardiac stimulation device comprising:
a first sensing circuit that senses atrial activity of a heart; and
a pulse generator that, responsive to the first sensing circuit sensing an AF episode, delivers a first plurality of stimulation pulses to the AV node of the heart at a beginning of an AV nodal refractory period following the sensed AF episode;
wherein the pulse generator is arranged to provide the stimulation pulses with an energy above the atrial capture threshold of the heart to extend the AV nodal refractory period; and
wherein after the plurality of first stimulation pulses are delivered, a first atrial event of a next cardiac cycle is sensed and a time period T2 is selected so that only a single atrial event occurs during that time period T2, and wherein if it is determined that the AF episode is not terminated, the pulse generator delivers a second plurality of stimulation pulses to the AV node of the heart at the completion of the time period T2.

5. The device of claim 4, wherein the pulse generator is arranged to provide the plurality of stimulation pulses during an interval having a duration related to a desired ventricular rate of the heart.

6. The device of claim 5, further comprising a second sensing circuit that senses ventricular activity of the heart to monitor ventricular rate.

7. The device of claim 4, wherein a frequency of the stimulation pulses to the AV node is slightly higher than 1/AVRP.

* * * * *